(12) United States Patent
Waldmann et al.

(10) Patent No.: US 11,272,297 B2
(45) Date of Patent: Mar. 8, 2022

(54) INTRA-OPERATIVE DETERMINATION OF VIBRATORY COUPLING EFFICIENCY

(71) Applicant: Cochlear Limited, Macquarie University (AU)

(72) Inventors: Bernd Waldmann, Hannover (DE); Tiago Rocha Felix, Hannover (DE)

(73) Assignee: Cochlear Limited, Macquire University (AU)

( * ) Notice: Subject to any disclaimer, the term of this patent is extended or adjusted under 35 U.S.C. 154(b) by 6 days.

(21) Appl. No.: 16/969,369

(22) PCT Filed: Feb. 6, 2019

(86) PCT No.: PCT/IB2019/050944
§ 371 (c)(1),
(2) Date: Aug. 12, 2020

(87) PCT Pub. No.: WO2019/159037
PCT Pub. Date: Aug. 22, 2019

(65) Prior Publication Data
US 2021/0051418 A1    Feb. 18, 2021

Related U.S. Application Data

(60) Provisional application No. 62/629,747, filed on Feb. 13, 2018.

(51) Int. Cl.
*H04R 25/00* (2006.01)
(52) U.S. Cl.
CPC ........... *H04R 25/30* (2013.01); *H04R 25/606* (2013.01); *H04R 2225/39* (2013.01)
(58) Field of Classification Search
CPC ...... H04R 25/70; H04R 25/30; H04R 25/606; H04R 25/305; H04R 2225/025;
(Continued)

(56) References Cited

U.S. PATENT DOCUMENTS

| | | | |
|---|---|---|---|
| 7,137,946 B2 | 11/2006 | Waldmann | |
| 2002/0026091 A1* | 2/2002 | Leysieffer | H04R 25/407 600/25 |

(Continued)

FOREIGN PATENT DOCUMENTS

WO    98/36711 A1    8/1998

OTHER PUBLICATIONS

International Search Report and Written Opinion received in international app No. PCT/IB2019/050944 dated Jun. 7, 2019 (16 pages).

(Continued)

*Primary Examiner* — Norman Yu
(74) *Attorney, Agent, or Firm* — Edell, Shapiro & Finnan, LLC

(57) ABSTRACT

Presented herein are directed to techniques for using objective measurements to determine a combined efficiency of an implantable actuator and a mechanical coupling of the implantable actuator to an auditory structure of an ear of a recipient. In particular, the implantable actuator is activated so as to deliver, via the mechanical coupling, mechanical stimulation to the auditory structure to effect a pressure change in an inner ear of the recipient. At least one stimulation device, that is separate from the implantable actuator, is configured to deliver secondary stimulation to the recipient to also effect a pressure change in the inner ear of the recipient. Objective measurements are performed to intra-operatively capture auditory evoked responses of the recipient in response to the mechanical stimulation and in response to the secondary stimulation. These auditory evoked responses are analyzed to determine a vibratory coupling efficiency.

29 Claims, 9 Drawing Sheets

(58) Field of Classification Search
CPC ............ H04R 2460/03; H04R 2225/67; H04R 25/356; H04R 1/1016; H04R 2225/39
USPC ....... 381/60, 320, 23.1, 56–57, 58, 328, 104
See application file for complete search history.

(56) References Cited

U.S. PATENT DOCUMENTS

| | | |
|---|---|---|
| 2002/0062059 A1 | 5/2002 | Waldmann |
| 2003/0163022 A1 | 8/2003 | Miller |
| 2006/0247488 A1* | 11/2006 | Waldmann ............. H04R 25/30 600/25 |
| 2011/0190882 A1* | 8/2011 | Parker .................... H04R 25/00 623/10 |
| 2015/0360028 A1* | 12/2015 | Tsampazis ........... H04R 25/606 607/57 |
| 2016/0059015 A1 | 3/2016 | Risi |
| 2017/0347209 A1 | 11/2017 | Heasman |

OTHER PUBLICATIONS

Geiger et al., "Klinische Studie zu BERA Messungen über die Vibrant Soundbridge und miniTek mittels optimierten Chirpreizen und klinischem Hörerfeolg," 21 Jahrestagung der Deutschen Gesellschaft für Audiologie, 2017 (2 pages).

Extended European Search Report in counterpart European Application No. 19754686.4-1210, dated Sep. 27, 2021, 13 pages.

Lee, JangWoo et al., "Comparison of auditory responses determined by acoustic stimulation and by mechanical round window stimulation at equivalent stapes velocities," Hearing Research, Elsevier Science Publishers, Amsterdam, NL, vol. 314, Apr. 24, 2014, 7 pages.

\* cited by examiner

DELIVERING, WITH AN IMPLANTABLE ACTUATOR IMPLANTED IN A RECIPIENT AND COUPLED TO AN AUDITORY STRUCTURE OF AN EAR OF THE RECIPIENT, MECHANICAL STIMULATION TO THE AUDITORY STRUCTURE TO EFFECT A PRESSURE CHANGE IN AN INNER EAR OF THE RECIPIENT — 352

CAPTURING ONE OR MORE FIRST AUDITORY EVOKED RESPONSES OF THE RECIPIENT TO THE MECHANICAL STIMULATION — 354

DELIVERING, WITH ONE OR MORE STIMULATION DEVICES THAT ARE SEPARATE FROM THE IMPLANTABLE ACTUATOR, SECONDARY STIMULATION TO THE RECIPIENT TO EFFECT A PRESSURE CHANGE IN THE INNER EAR OF THE RECIPIENT — 356

CAPTURING ONE OR MORE SECOND AUDITORY EVOKED RESPONSES OF THE RECIPIENT TO THE SECONDARY STIMULATION — 358

DETERMINING, USING THE ONE OR MORE FIRST AND ONE OR MORE SECOND AUDITORY EVOKED RESPONSES, AN EFFICIENCY OF THE IMPLANTABLE ACTUATOR AND THE COUPLING TO THE AUDITORY STRUCTURE — 360

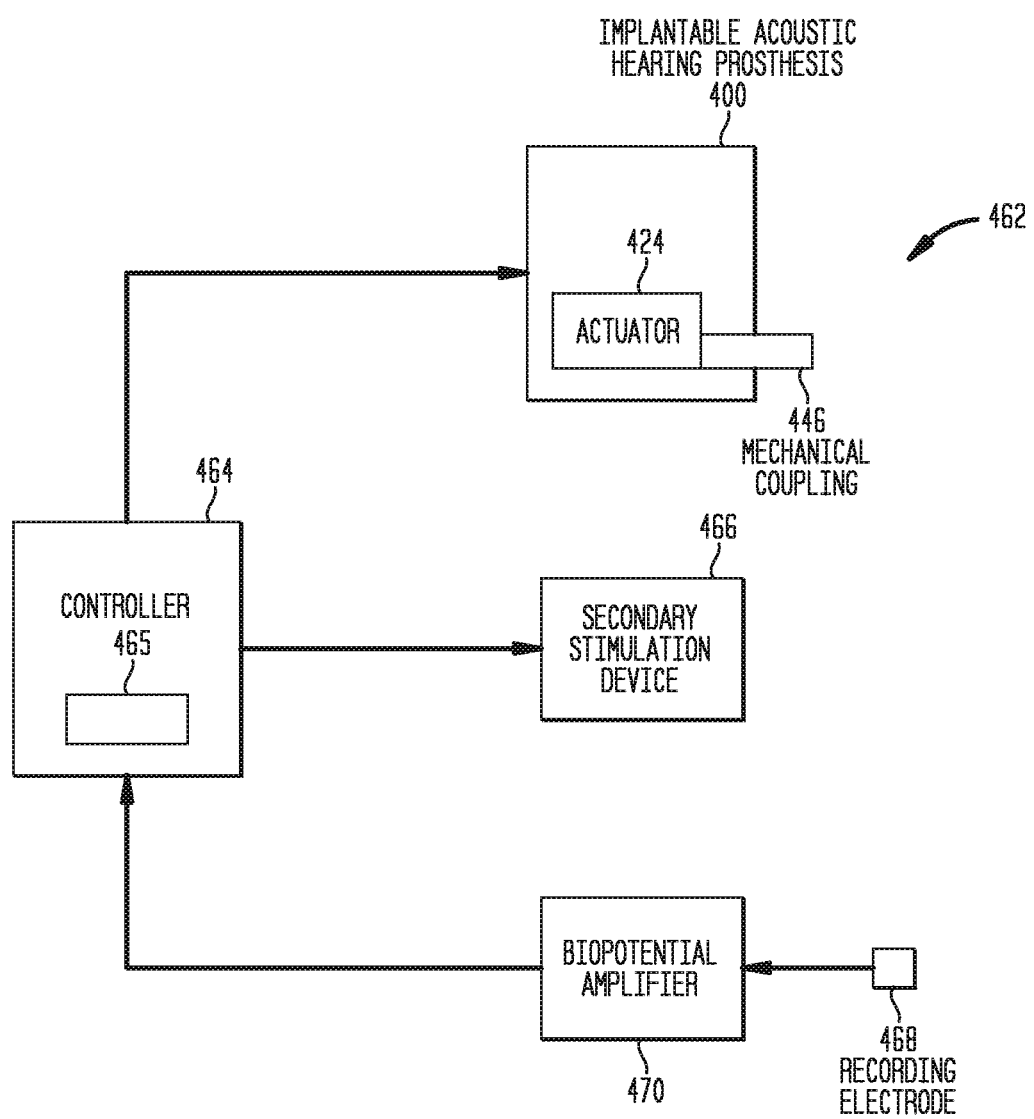

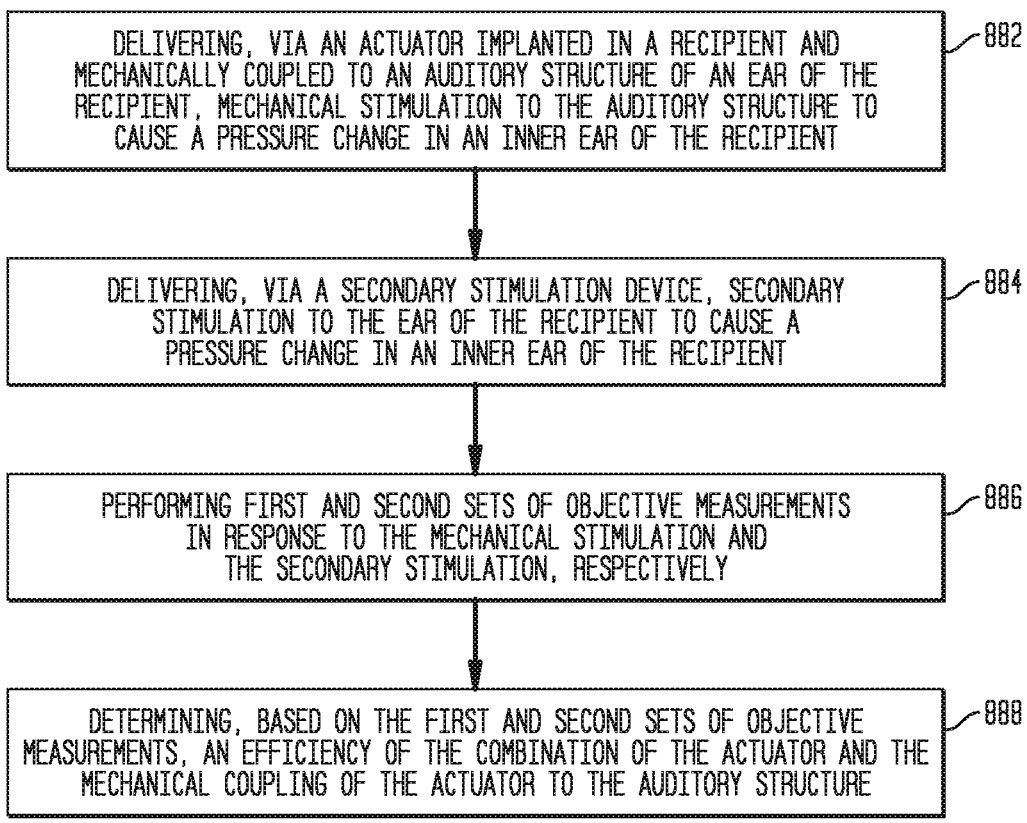

INTRA-OPERATIVE DETERMINATION OF VIBRATORY COUPLING EFFICIENCY

BACKGROUND

Field of the Invention

Certain aspects presented herein relate generally to the use of intra-operative measurements to determine vibratory coupling efficiency in an implantable hearing prosthesis.

Related Art

Hearing loss, which may be due to many different causes, is generally of two types: conductive and sensorineural. Sensorineural hearing loss is due to the absence or destruction of the hair cells in the cochlea that transduce sound signals into nerve impulses. Various auditory or hearing prostheses are commercially available to provide individuals suffering from sensorineural hearing loss with the ability to perceive sound.

Conductive hearing loss occurs when the normal mechanical pathways that provide sound to hair cells in the cochlea are impeded, for example, by damage to the ossicular chain or ear canal. Individuals suffering from conductive hearing loss may retain some form of residual hearing because the hair cells in the cochlea may remain undamaged. Conductive hearing loss may be treated in a number of manners, including through the use of one or more acoustic hearing aids, bone conduction devices, implantable acoustic hearing prostheses (sometimes referred to as a middle ear implants, acoustic prostheses, or acoustic implants), etc.

Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing pressure waves in the perilymph that evoke the generation of nerve impulses, which result in the perception of the received sound. An implantable acoustic hearing prosthesis converts received sound signals into mechanical forces that are applied to an auditory structure of a recipient's ear, such as the ossicular chain or directly to the cochlea, via an actuator/transducer implanted in or adjacent to the middle ear cavity. The mechanical forces cause pressure changes in the inner ear that evoke the generation of nerve impulses, which result in the perception of the received sound signals.

SUMMARY

In one aspect, a method is provided. The method comprises: delivering, with an actuator implanted in a recipient and mechanically coupled to an auditory structure of an ear of the recipient, mechanical stimulation to the auditory structure to effect a pressure change in an inner ear of the recipient; capturing one or more first auditory evoked responses of the recipient to the mechanical stimulation; delivering, with one or more stimulation devices that are separate from the actuator, secondary stimulation to the recipient to effect a pressure change in the inner ear of the recipient; capturing one or more second auditory evoked responses of the recipient to the secondary stimulation; and determining, using the one or more first auditory evoked responses and the one or more second auditory evoked responses, an efficiency of a combination of the actuator and the mechanical coupling of the actuator to the auditory structure.

In another aspect, a system is provided. The system comprises: an actuator implanted in a recipient and mechanically coupled to an auditory structure of an ear of the recipient, wherein the actuator is configured to deliver mechanical stimulation to the auditory structure to cause a pressure change in an inner ear of the recipient; a secondary stimulation device configured to deliver secondary stimulation to the ear of the recipient to cause a pressure change in an inner ear of the recipient; at least one recording electrode and at least one biopotential amplifier configured to capture a first set of auditory evoked responses evoked at the inner ear of the recipient in response to the mechanical stimulation and to capture a second set of auditory evoked responses associated with the inner ear of the recipient and evoked in response to the secondary stimulation; and a controller configured to determine, using the first and second sets of auditory evoked responses, an equivalent sound pressure level associated with operation of the actuator.

In another aspect, a method is provided. The method comprises: delivering, via an actuator implanted in a recipient and mechanically coupled to an auditory structure of an ear of the recipient, mechanical stimulation to the auditory structure to cause a pressure change in an inner ear of the recipient; delivering, via a secondary stimulation device, secondary stimulation to the ear of the recipient to cause a pressure change in an inner ear of the recipient; performing first and second sets of objective measurements evoked in response to the mechanical stimulation and the secondary stimulation, respectively; and determining, based on the first and second sets of objective measurements, a combined efficiency of the actuator and the mechanical coupling of the actuator to the auditory structure.

BRIEF DESCRIPTION OF THE DRAWINGS

Embodiments of the present invention are described herein in conjunction with the accompanying drawings, in which:

FIG. 3 is a flowchart illustrating a method, in accordance with certain embodiments presented herein;

FIG. 4 is block diagram illustrating a system, in accordance with certain embodiments presented herein;

FIG. 8 is a flowchart illustrating another method, in accordance with certain embodiments presented herein.

DETAILED DESCRIPTION

Certain embodiments presented herein are directed to techniques for using objective measurements to determine a combined efficiency of an implantable actuator and a mechanical coupling of the implantable actuator to an auditory structure of an ear of a recipient. For example, in some embodiments the implantable actuator is activated so as to deliver, via the mechanical coupling, mechanical stimulation to the auditory structure to effect a pressure change in an inner ear of the recipient. At least one stimulation device, that is separate from the implantable actuator, is configured to deliver secondary stimulation to the recipient to also effect a pressure change in the inner ear of the recipient. Objective measurements are performed to intra-operatively capture auditory evoked responses of the recipient in response to the mechanical stimulation and in response to the secondary stimulation. These auditory evoked responses are analyzed to determine a vibratory coupling efficiency (e.g., an efficiency of the actuator in combination with the associated mechanical coupling of the actuator to the auditory structure).

Merely for ease of illustration, the techniques presented herein will generally be described with reference to implantable actuators forming part of implantable acoustic hearing prostheses. As used herein and as described further below, an implantable acoustic hearing prosthesis may be a semi-implantable acoustic hearing prosthesis, a mostly-implantable acoustic hearing prosthesis, or a totally-implantable acoustic hearing prosthesis. It is to be appreciated that these examples are illustrative and that the techniques presented herein can be implemented with a number of other types of implantable hearing prostheses that include an implantable actuator, such as electro-acoustic hearing prostheses, bimodal hearing prostheses, etc.

Figure 1A:
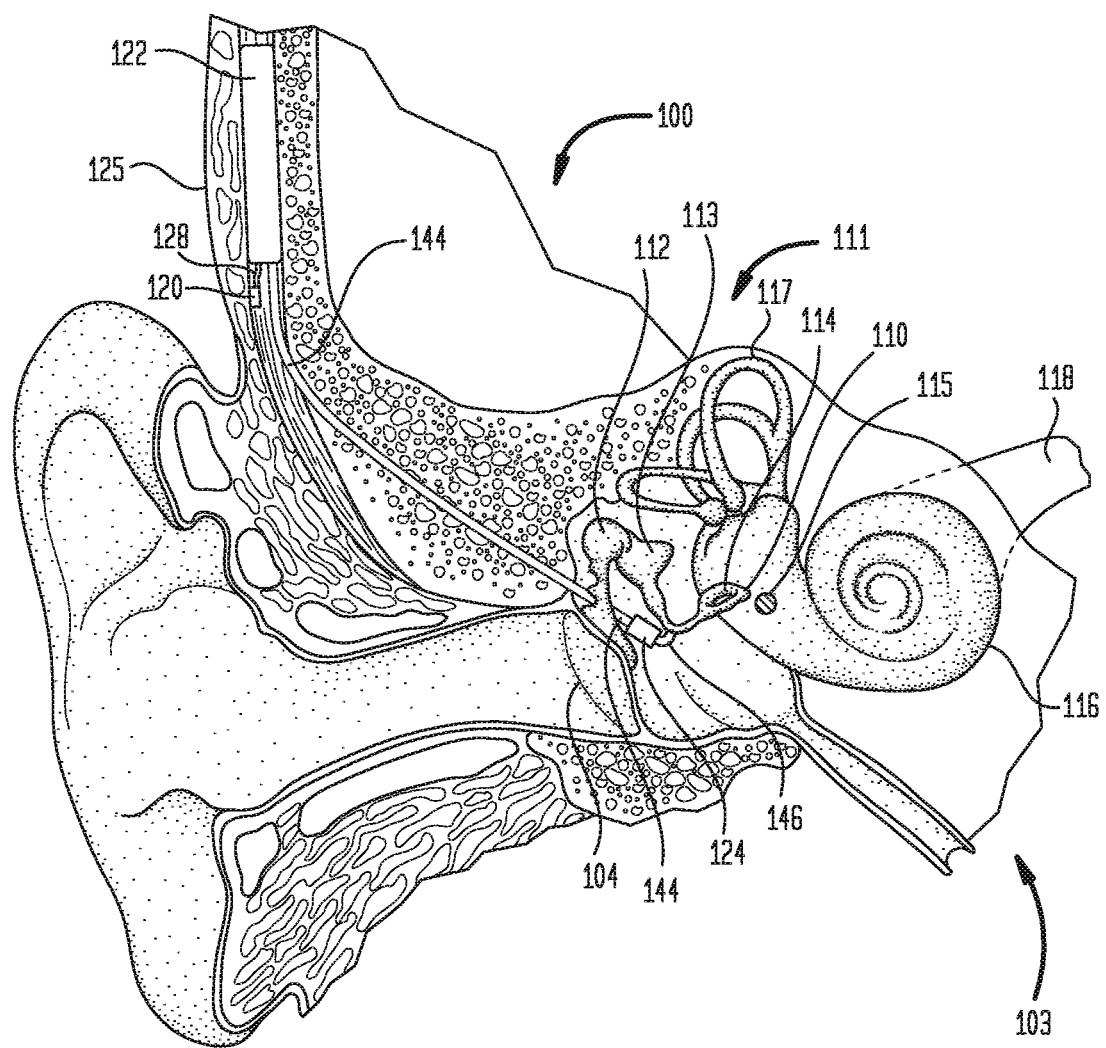
FIG. 1A is a schematic diagram illustrating a totally-implantable acoustic hearing prosthesis, in accordance with certain embodiments presented herein.
Figure 1B:
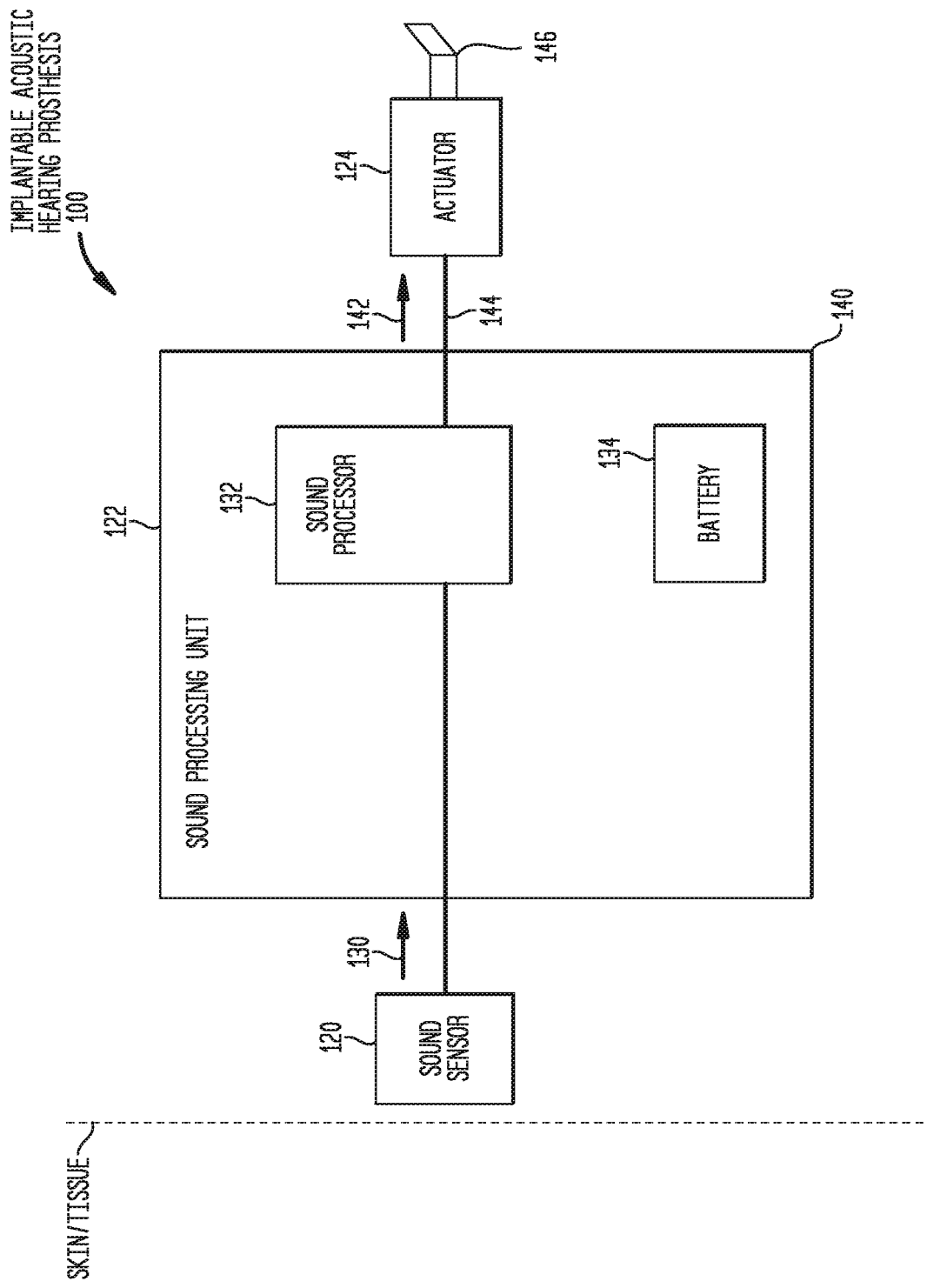
FIG. 1B is a schematic diagram illustrating a totally-implantable acoustic hearing prosthesis, in accordance with certain embodiments presented herein.

FIG. 1A is a schematic diagram illustrating an implantable acoustic hearing prosthesis 100 in accordance with certain embodiments presented herein. FIG. 1B is a block diagram of the implantable acoustic hearing prosthesis 100. For ease of description, FIGS. 1A and 1B will be described together.

The implantable acoustic hearing prosthesis 100 is, in general, configured to convert sound signals entering the recipient's outer ear into mechanical vibrations that are directly or indirectly transferred to the cochlea 116, thereby causing generation of nerve impulses that result in the perception of the received sound. The implantable acoustic hearing prosthesis 100 comprises a sound sensor 120, a sound processing unit 122, and an implantable actuator/transducer 124 all implanted in the head 125 of the recipient. Since all components of the implantable acoustic hearing prosthesis 100 are implanted within the head 125 of the recipient, the implantable acoustic hearing prosthesis 100 can be referred to as a "totally-implantable" acoustic hearing prosthesis. Although not shown in FIGS. 1A and 1B, the sound sensor 120 and the actuator 124 can each include hermetically-sealed housings.

FIG. 1A illustrates an example in which the sound sensor 120 is a subcutaneous microphone. However, it is to be appreciated that this specific configuration is illustrative and that a variety of different sound sensors and locations may be used in accordance with certain embodiments presented herein. For example, in alternative embodiments, the implantable acoustic hearing prosthesis 100 could include a sound sensor coupled to an auditory element of the recipient's ear that vibrates in response to receipt of sound signals, such as the tympanic membrane 104, the ossicles 111 (e.g., one or more of the malleus 112, the incus 113 or the stapes 114), the oval window 110, the recipient's round window 115, semicircular canals 117, etc. In other embodiments, the implantable acoustic hearing prosthesis 100 may also or alternatively include an external sound sensor. In such embodiments, an external sound sensor could be worn by the recipient, located at or in the outer ear, etc. and the received sound signals could be transcutaneously transferred to the sound processing unit 122.

As shown in FIG. 1B, the sound processing unit 122 comprises a sound processor 132 and at least one battery 134 each disposed in a hermetically-sealed housing 140. The at least one battery 134 is configured to supply power to the other components of the implantable acoustic hearing prosthesis 100. For ease of illustration, connections between the at least one battery 134 and the various powered components of the implantable acoustic hearing prosthesis 100 have been omitted from FIG. 1B. It is also to be appreciated that the specific arrangement for sound processing unit 122 shown in FIG. 1B is illustrative and that the sound processing unit 122 could include other elements, such as a radio frequency (RF) coil, RF interface circuitry, a wireless interface, etc. that, for ease of illustration, have been omitted from FIG. 1B.

In the examples of FIGS. 1A and 1B, the sound processor 132 receives the electrical signals 130 from the sound sensor 120. In response, the sound processor 132 processes (e.g., adjusts amplifies, etc.) the received electrical signals 130 according to the hearing needs of the recipient. That is, the sound processor 132 converts the electrical signals 130 into processed signals 142. The processed signals 142 generated by the sound processor 134 are then provided to the actuator 124 via a lead 144. That is, the processed signals 142 are used to activate/actuate or drive the actuator 124 to generate mechanical stimulation (e.g., vibrations for delivery to an auditory element of the hearing anatomy of the recipient).

Actuators, such as actuator 124, of an implantable hearing prosthesis are mechanically coupled to an auditory element of the recipient's ear such that generated mechanical stimulation effects/causes pressure changed within the inner ear of the recipient. For example, in the embodiment of FIGS. 1A and 1B, the actuator 124 is mechanically coupled to the stapes 114 via a coupling element 146. As such, the coupling element 146 relays the vibration generated by the actuator 124 to the stapes 114 which, in turn, causes oval window 110 to vibrate. Such vibration of the oval window 110 sets up pressure waves within the cochlea 116 which, in turn, activate hair cells (not shown) that line the inside of the cochlea 116. Activation of these hair cells causes appropriate nerve impulses to be transferred through the spiral ganglion cells and the auditory nerve 118 to the brain (not shown), where they are perceived as sound.

FIGS. 1A and 1B generally illustrate an implantable acoustic hearing prosthesis 100 in which the actuator 124 is mechanically coupled to an element of the recipient's middle ear (e.g., the stapes 114). As such, FIGS. 1A and 1B generally illustrate an example embodiment in which the actuator 124 is indirectly coupled to the inner ear 103. It is to be appreciated that, in alternative embodiments, an actuator may be directly coupled to the inner ear 103.

Figure 2:
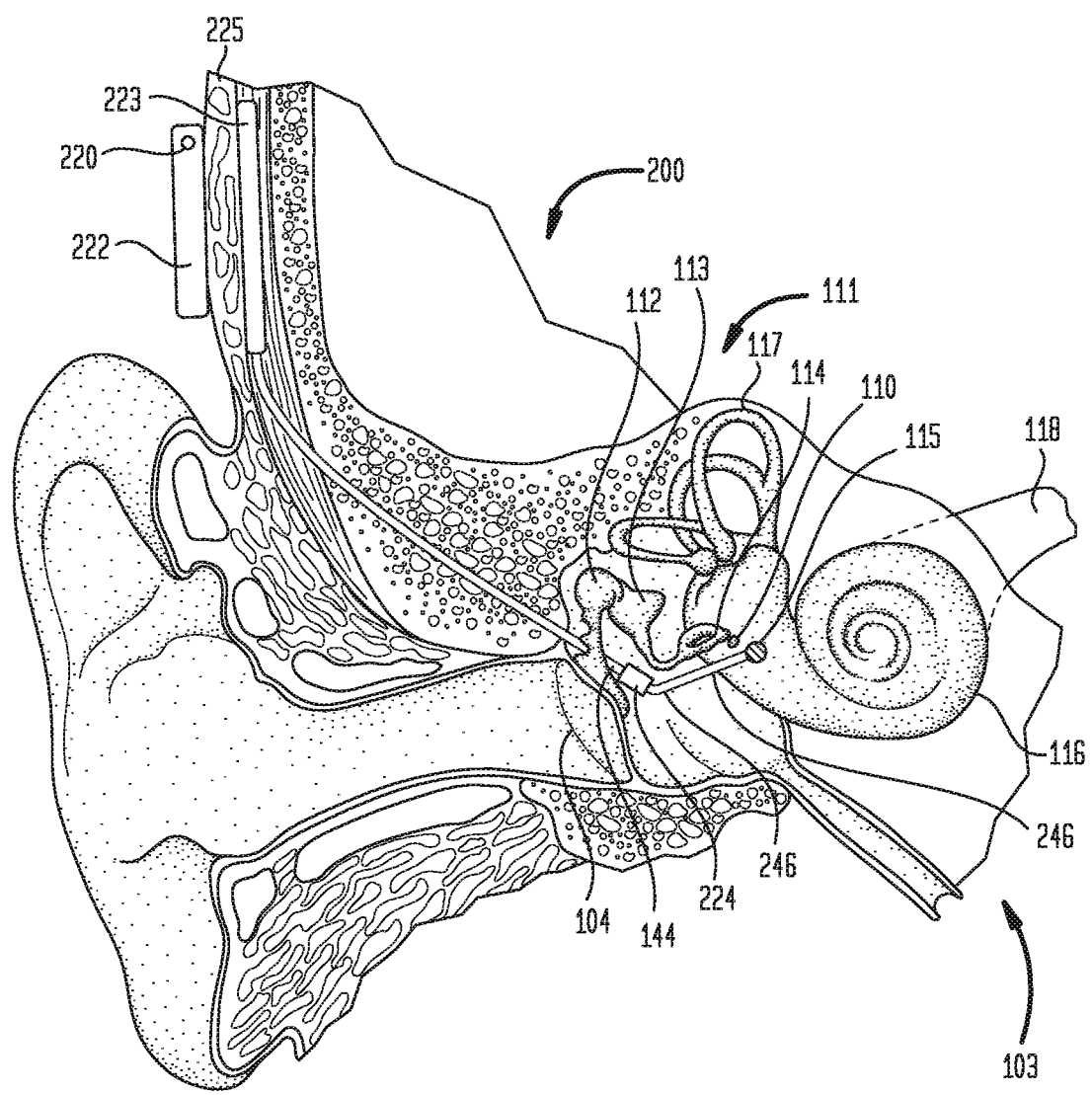
FIG. 2 is a schematic diagram illustrating a semi-implantable acoustic hearing prosthesis, in accordance with certain embodiments presented herein.

For example, FIG. 2 is a schematic diagram illustrating an implantable acoustic hearing prosthesis 200 whereby the actuator is directly coupled to the inner ear 103 in accordance with other embodiments presented herein. Similar to the arrangement of FIGS. 1A and 1B, the implantable acoustic hearing prosthesis 200 is, in general, configured to convert sound signals entering the recipient's outer ear into mechanical vibrations that are directly or indirectly transferred to the cochlea 116, thereby causing generation of nerve impulses that result in the perception of the received sound.

In the embodiments of FIG. 2, the implantable acoustic hearing prosthesis 200 includes a sound sensor 220, a sound processing unit 222, an implant body 223, and an implantable actuator/transducer 224. The sound sensor 220 and the sound processing unit 222 are external components configured to be coupled to, or worn by, the recipient, while the implant body 223 and the actuator 224 are implanted in the head 225 of the recipient. Since only some of the components of the implantable acoustic hearing prosthesis 200 are implanted within the head 225 of the recipient, the implantable acoustic hearing prosthesis 200 can be referred to as a "semi-implantable" acoustic hearing prosthesis. Although not shown in FIG. 2, the actuator 224 can include a hermetically-sealed housing.

The sound processing unit 222 comprises a sound processor (not shown in FIG. 2) that converts sounds sensed by the sound sensor 220 into electrical signals that are transcutaneously transferred to the implant body 223 via a radio frequency (RF) link. The implant body 223 uses the electrical signals received from the sound processing unit 222 to drive the actuator 224. In the embodiment of FIG. 2, the actuator 224 is mechanically coupled to the round window 115 via a coupling element 246. As such, the coupling element 246 relays the vibration generated by the actuator 224 to the round window 115, which in turn, causes round window 115 to vibrate. In an alternate embodiment, the actuator 224 could be coupled to the oval window 110, an opening in the semicircular canals 117, directly to an implant element reaching into the cochlear fluid, or another structure of the inner ear 103.

Collectively, FIGS. 1A, 1B, and 2 illustrate various arrangements for implantable acoustic hearing prostheses. As noted, these arrangements are merely examples and that the embodiments presented herein may be implemented in totally-implantable acoustic hearing prostheses, mostly-implantable acoustic hearing prostheses, semi-implantable acoustic hearing prostheses, and/or other types hearing prostheses. However, in accordance with the various embodiments presented herein, an implantable actuator is either directly or indirectly coupled to the inner ear of recipient to deliver mechanical stimulation (vibration) thereto. As a result, the actuator, in combination with the associated mechanical coupling of the actuator to the auditory structure (e.g., the middle ear bones, inner ear, etc.), have an associated overall "efficiency," which is sometimes referred herein as the "vibratory coupling efficiency." As used herein, the "vibratory coupling efficiency," or the efficiency of the actuator in combination with the associated mechanical coupling of the actuator to the auditory structure, can be understood to refer to how well the actuator and mechanical coupling operate to convert a given drive signal (e.g., voltage, current, etc.) received at the actuator into mechanical vibration at the inner ear and, therefore, into loudness sensation. As such, the vibrating coupling efficiency can be understood to be a function of the efficiency of the mechanical coupling as well as a function of the inherent efficiency of the actuator.

The vibratory coupling efficiency (e.g., efficiency of the combination of the actuator and associated mechanical coupling of the actuator to the auditory structure) can have a direct impact on clinical outcomes of the recipient because the efficiency determines (limits), for a given electrical gain and maximum electrical output, the maximum gain and output level achievable with the implantable acoustic hearing prosthesis. The maximum gain and output level achievable with the implantable acoustic hearing prosthesis in turn determines the degree of speech recognition performance the recipient can achieve. In other words, the gain of the implantable acoustic hearing prosthesis, from the sound sensor(s) (either implanted or non-implanted) to the creation of a loudness sensation at the output can be significantly affected by the efficiency of the coupling between the actuator and the auditory structure of the ear. However, in conventional arrangements the post-implantation mechanical coupling tends to be variable, which in turn leads to inconsistent clinical outcomes, additional surgeries, etc. Therefore, being able to intra-operatively (e.g., during the implantation process and before closing the incision) predict the vibratory coupling efficiency, and thus the likely clinical performance is beneficial to surgeons and recipients as it can enable optimal mechanical coupling between the actuator and the auditory structure during the initial surgery.

Presented herein are intra-operative techniques for providing a surgeon or other user with an indication of the vibratory coupling efficiency (e.g., the efficiency of the combination of the actuator and the mechanical coupling of the actuator to the ossicular chain or cochlea). More specifically, in many embodiments presented herein, the implantable actuator is activated so as to deliver, via the mechanical coupling, mechanical stimulation to the auditory structure of the recipient to effect/cause a pressure change in an inner ear of the recipient. At least one secondary stimulation device, which is separate from the implantable actuator, is configured to deliver secondary stimulation to the recipient to also effect a pressure change in the inner ear of the recipient. The secondary stimulation is delivered via a pathway (e.g., sound in air or skull vibration) that is separate/different from the actuator and mechanical coupling and for which calibrated stimulus levels are available. For example, with sound in air, it is possible to convert sound pressure (dB SPL) to normal hearing level dB HL via American National Standards Institute (ANSI) standards, while with skull vibration it is possible to: convert force levels to dB HL, also via ANSI or ISO standards.

Intra-operative objective measurements can be performed to capture auditory evoked responses/potentials of the recipient in response to the mechanical stimulation and in response the secondary stimulation. The auditory evoked responses can be analyzed to determine an efficiency of the combination of the implantable actuator and the mechanical coupling of the actuator to the auditory structure. As a result, some embodiments presented herein may provide the surgeon with intra-operative objective feedback (e.g., before finishing implantation) regarding the likely clinical outcomes for the recipient of the implantable acoustic hearing prosthesis.

FIG. 3 is a high level flowchart of a method 350 in accordance with certain embodiments presented herein. For ease of illustration, method 350 of FIG. 3 will be described without making reference to any specific devices. Example devices for performing the method 350 of FIG. 3 are described below with reference to FIGS. 4-6. In the example of FIG. 3, an implantable actuator is implanted in a recipient and is mechanically coupled to an auditory structure of the recipient's ear, such as the ossicles (e.g., one or more of the malleus, the incus, or the stapes), the oval window, the round window, semicircular canals, etc.

Method 350 begins at 352 where the implantable actuator, which is implanted in a recipient and mechanically coupled to the auditory structure, is activated to deliver mechanical stimulation to the auditory structure. The mechanical stimulation causes/effects a pressure change in an inner ear of the recipient. To generate the mechanical stimulation, the actuator is driven at a known level (e.g., a known driving voltage, current, power, etc. is provided to the actuator). In certain embodiments, the known level may be a voltage expressed, for example, in Volts or dBV, where dBV is a logarithmic voltage ratio in decibels (dB) with a reference voltage of dBV corresponding to a voltage of 1 V.

At 354, one or more first auditory evoked responses of the recipient, which are evoked by the mechanical stimulation, are captured using one or more objective measurements. The one or more first auditory evoked responses may include, for example, electrocochleography (ECoG) responses or electrically evoked compound action potentials (ECAPs), such as the cochlear microphonic, higher evoked potential measurements from the brainstem and auditory cortex, or other responses/potentials/signals evoked at an auditory structure in response to the delivered mechanical stimulation. As such, the one or more first auditory evoked responses may include signals captured as a result of any measurement of any physiological feature that can enable the teachings detailed herein.

At 356, one or more secondary stimulation devices, which are different/separate from the implantable actuator, deliver secondary stimulation to the recipient so as to also effect a pressure change in the inner ear of the recipient. This secondary stimulation may comprise, for example, acoustic stimulation airborne sound (e.g., acoustic signals delivered through the ear canal), bone conduction (e.g., vibration delivered directly or indirectly to the skull of the recipient), etc. The separate secondary stimulation occurs at a known hearing level expressed, for example, in decibel Hearing Level (dB HL) or a known sound pressure level expressed, for example, in decibel Sound Pressure Level (dB SPL) or pascal (Pa).

In accordance with embodiments presented herein, the secondary stimulation may be delivered in a number of different manners using a number of different stimulation devices. For example, in certain embodiments presented herein, the secondary stimulation comprises acoustic signals delivered via an insert ear phone in the ear canal. In other embodiments, the secondary stimulation comprises acoustic signals delivered via a receiver (e.g., loudspeaker) positioned at, in, or near the recipient's outer ear. In still other embodiments, the secondary stimulation comprises vibration (bone conduction) delivered via a bone vibrator (e.g., attached to the patient's forehead or mastoid).

At 358, one or more second auditory evoked responses of the recipient, which are evoked by the secondary stimulation, are captured using one or more objective measurements. In general, the captured one or more second auditory evoked responses are the same type of signals as the first auditory evoked responses, but have been evoked in a different manner.

At 360, a vibratory coupling efficiency (e.g., an efficiency of the combination of the implantable actuator and of the mechanical coupling of the actuator to the auditory structure) is determined using the one or more first and one or more second auditory evoked responses. More specifically, in certain embodiments, a determination/calculation is made as to the sound pressure level (hearing level) where a parameter of at leak one of the one or more second auditory evoked responses (e.g., evoked in response to the secondary stimulation) has the same value as a parameter of at least one of the one or more first auditory evoked responses (e.g., evoked in response to the actuator-provided mechanical stimulation at a given voltage level). This determined sound pressure level is referred to here as the "equivalent sound pressure level" for the implanted actuator and the associated mechanical coupling to the auditory structure of the ear. The equivalent sound pressure level can be analyzed/evaluated to determine the efficiency of the combination of the implanted actuator and the associated mechanical coupling of the actuator to the auditory structure. For example, using the second auditory evoked responses as a reference, the vibratory coupling efficiency can be calculated in terms of a dBV value that provides the same loudness as a dB SPL value.

In certain embodiments, the equivalent sound pressure level and/or the determined efficiency can be compared to normative data obtained from a larger population of recipients to provide an indication of a "relative" vibratory coupling efficiency (e.g., a measure indicating how the calculated vibratory coupling efficiency compares to other recipients with the same implantable hearing prosthesis). For example, the equivalent sound pressure level and/or the determined efficiency could be compared to a predetermined normative threshold level (e.g., a level determined from data associated with other recipients) to determine if the vibratory coupling efficiency is acceptable for the recipient.

Many different attributes/parameters of the first and second auditory evoked responses may be analyzed (e.g., compared) to determine the equivalent sound pressure level and the relative efficiency of the implanted actuator (e.g., equivalency between the mechanical stimulation delivered via the actuator and the secondary stimulation is determined using the recorded response amplitudes). For example, in certain embodiments, amplitude parameters of the first and second auditory evoked responses (e.g., amplitude of captured cochlear microphonic signals) may be used to establish the equivalent sound pressure level. In other embodiments, latency parameters of the first and second auditory evoked responses may be used to establish the equivalent sound pressure level. In one specific such example, the latency refers to the timing of the auditory brainstem response where a lower latency is correlated to louder signals and a longer latency is correlated to lower/softer signal. It is to be appreciated that, in further embodiments, morphological properties related to the width of activation and coupling across frequencies may also or alternatively be analyzed. It is also to be appreciated that a given analysis may consider one, or multiple types of parameters, to determine the equivalent sound pressure level and vibratory coupling efficiency.

In general, the equivalent sound pressure level and/or vibratory coupling efficiency is used to provide intra-operative feedback to a surgeon or other user. For example, in certain embodiments, the intra-operative feedback may be an audible or visible indication of the determined equivalent sound pressure level and/or vibratory coupling efficiency. In further embodiments, the intra-operative feedback may be an audible or visible indication of the relative quality of vibratory coupling efficiency relative to normative data (e.g., "Vibratory coupling efficiency is better that the 75% percentile of prior recipients," "Vibratory coupling efficiency is 10 dB worse than the average," "Vibratory coupling efficiency is 10 dB better than the average," and so on).

In certain embodiments, the equivalent sound pressure level and/or vibratory coupling efficiency estimate or predict clinical outcomes for the recipient. For example, the equivalent sound pressure level and/or vibratory coupling efficiency estimate can be used to calculate the maximum gain and output level that the implantable acoustic hearing prosthesis will provide. The maximum gain and output level that the implantable acoustic hearing prosthesis can be assessed to determine whether that gain and output will be sufficient to satisfy the audiological needs of the recipient, for example, in terms of achieving audibility for desired speech signals, in terms of providing enough dynamic range to the auditory pathway, etc. This information may also be provided in an audible or visible indication to the recipient (e.g., "With this coupling, MPO of x dB SPL can be achieved").

FIG. 3 illustrates an example embodiment in which the mechanical stimulation is delivered prior to (before) the secondary stimulation. It is to be appreciated that the specific order of stimulation shown in FIG. 3 is illustrative and that, in alternative embodiments, the secondary stimulation may be delivered prior to the mechanical stimulation, simultaneously with the mechanical stimulation, etc. For example, the mechanical stimulation and secondary stimulation, and the associated recordings of auditory evoked responses, could occur simultaneously at slightly different frequencies or occur in an interleaved manner (e.g., alternating tone bursts via mechanical stimulation and secondary stimulation), etc.

In summary, FIG. 3 illustrates embodiments in which objective measurements are performed to obtain auditory evoked responses in response to both mechanical stimulation via an implanted actuator and in response to separate secondary stimulation, such as through audiometric equipment, a bone conduction device, etc. Based on the evoked potentials, an equivalent sound pressure level (e.g., the sound pressure where an evoked potential response parameter in response to the secondary stimulation has the same value as with an actuator stimulation at a given voltage level) is determined and analyzed to determine the efficiency of the combination of the implanted actuator and the associated mechanical coupling of the actuator to the auditory structure.

In certain embodiments, using the information related to, or derived from, the efficiency of the combination of the implanted actuator and the associated mechanical coupling of the actuator to the auditory structure, a surgeon could determine whether the estimated operation of the implantable hearing prosthesis, given the determined vibratory coupling efficiency, is acceptable for the specific recipient. For example, required gains may be different for recipients having different hearing loss levels. As such, certain actuator-coupling efficiencies may be acceptable for certain recipients, but unacceptable for other recipients. If the surgeon determines that estimated operation of the implantable hearing prosthesis is unacceptable, the surgeon may make one or more intra-operative adjustments to a change the efficiency of the device. For example, the surgeon could re-position the tip of the actuator or coupling element (e.g., relative to the target auditory structure of the ear).

The above illustrates that the ability to intra-operatively determine vibratory coupling efficiency using objective measurements and, accordingly, estimate clinical outcomes for a recipient, may address the variability in outcomes experienced during implantation of implantable acoustic hearing prosthesis in conventional arrangements. That is, the techniques presented herein may be used to make the surgical implantation of implantable acoustic hearing prostheses, and more generally devices that include an implantable actuator, more predictable and/or or more easily influenced during surgery.

To facilitate further understanding of the techniques presented, one specific example calculation of a vibratory coupling efficiency based on intra-operatively evoked potentials is provided below. In this specific example, the ear of a recipient is stimulated with secondary stimulation via an insert earphone (or bone vibrator) with a 1000 Hertz (Hz) tone at a level of 80 dB HL. As a result of this secondary stimulation, a cochlear microphonic (CM) response with an amplitude of 2 µV (−114 dBV) is captured. The stimulation level of 80 dB HL can be converted to dB SPL by using American National Standards Institute (ANSI) S S3.6, where at 1000 Hz the conversion factor is 4 dB. As such, 80 dB HL is equal to approximately 84 dB SPL.

Subsequently, the implantable actuator is driven to deliver mechanical stimulation at 1000 Hz, where the driving voltage is approximately 100 mV (−20 dBV). As a result of this mechanical stimulation, a CM response with an amplitude of 4 µV (−108 dBV) is captured. Because the CM response is expected to be linear, it is possible to calculate that with half the driving voltage (e.g., a drive voltage of 50 mV, which is approximately −26 dBV then approximately half the response amplitude (2 µV=−114 dBV) would be captured.

Given the above, it can be determined that the secondary stimulation (acoustic stimulation) at 84 dB SPL and mechanical vibration when the actuator is driven with a voltage of approximately −26 dBV, will evoke the same cochlear microphonic amplitude and would have likely created the same loudness sensation had the recipient been awake.

If −26 dBV drive is equivalent to 84 dB SPL, then 0 dBV (1V) drive would have been equivalent to the secondary stimulation level (e.g., 84 dB SPL) minus the actuator drive voltage (e.g., −26 dBV), which results on the vibratory coupling efficiency (e.g., 110 dB SPL). That is, in this specific example, the vibratory coupling efficiency or actuator output in is 110 dB SPL equivalent at 1V (110 dB SPLeq), which are the same units as defined in ASTM F2504 for cadaver measurements. The 110 dB SPLeq efficiency may be compared to, for example, published cadaver measurements, normative data, etc. to determine whether the vibratory coupling efficiency is acceptable (e.g., is this recipient is as good as the average of the published data, is this recipient better or worse than prior recipients, etc.).

In an alternative example, if the recipient's hearing loss had been more severe, then the CM response would have been smaller (e.g., 0.2 µV, 0.4 µV, etc.), but both the response to secondary stimulation and vibratory stimulus would have been smaller, and the final result of 110 dB SPL equivalent at 1V would have been the same.

The above example describes an intra-operative process. In certain examples, the techniques presented herein may be implemented post-operatively. For example, continuing the above example, two months after the surgery a bone conduction threshold of, for example, 50 dB HL (54 dB SPL) at 1000 Hz is measured. A direct threshold, using the implant as a signal generator and driving the actuator with a known voltage, a threshold of −55 dBV is measured. As a result, a loudness perception of "barely audible" is obtained for both stimulations, e.g. 54 dB SPL equivalent at −50 dBV, (e.g., 54−(−55)=109 dB SPLeq at 0 dBV (1V)). In general, although specific examples of how the method illustrated in FIG. 3 can be applied are given, it should be appreciated that the illustrated and discussed method can be applied in any of a variety of ways in accordance with embodiments of the invention.

Figure 5:
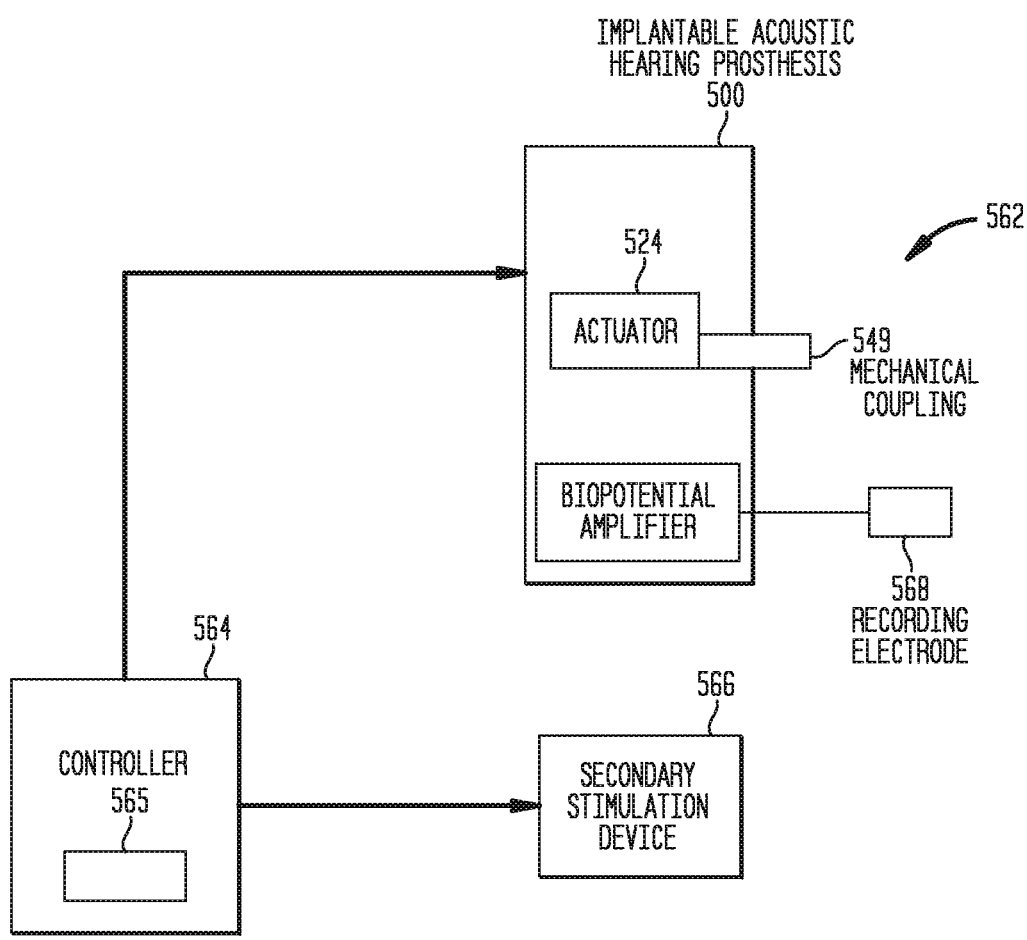
FIG. 5 is block diagram illustrating a system, in accordance with certain embodiments presented herein.
Figure 6:
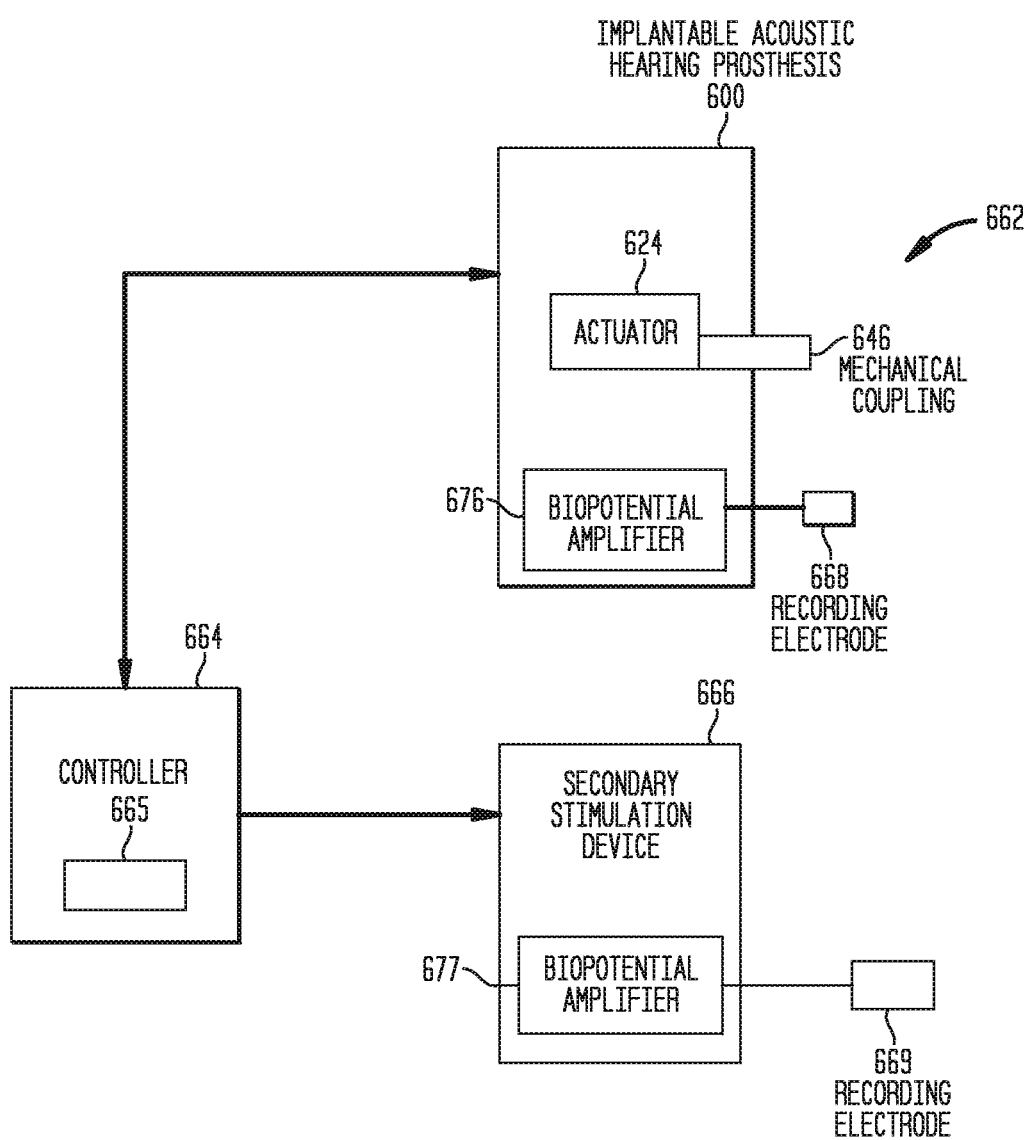
FIG. 6 is block diagram illustrating a system, in accordance with certain embodiments presented herein.

It is to be appreciated that the method 350 of FIG. 3, and other methods in accordance with certain embodiments presented herein, may be performed using a number of different devices/systems. FIGS. 4, 5, and 6 are schematic block diagrams illustrating functional components of example systems configured to implement techniques presented herein. It is to be appreciated that the connections between the various components shown in FIG. 4, 5, or 6 may be wired connections or wireless connections (e.g., using RF links).

Referring first to FIG. 4, shown is a system 462 that comprises a controller 464, an implantable acoustic hearing prosthesis 400, a secondary stimulation device 466, a recording electrode 468, and a biopotential amplifier 470. The implantable acoustic hearing prosthesis 400 includes an actuator 424 that is mechanically coupled to an auditory structure (not shown in FIG. 4) of a recipient's ear (also not shown in FIG. 4) via mechanical coupling 446. The controller 464 is, for example, a computing device that is configured to communicate (e.g., via wired or wireless connections) with the implantable acoustic hearing prosthesis 400, the secondary stimulation device 466, and the biopotential amplifier 470.

The controller 464 is configured to cause the implantable acoustic hearing prosthesis 400 to deliver mechanical stimulation to the auditory structure via the actuator 424 and the mechanical coupling 446 (e.g., the controller 464 causes/instructs the implantable acoustic hearing prosthesis 400 to drive the actuator 424 at a known voltage, current, power, etc.). As noted, the system 462 also comprises at least one recording electrode 468 and a biopotential amplifier 470. The recording electrode 468 is disposed in the recipient at a location that enables the recording electrode 468, and the biopotential amplifier 470, to record the first auditory evoked responses evoked at/in the recipient in response to the mechanical stimulation delivered via the actuator 424. In the embodiment of FIG. 4, the recorded first auditory evoked responses are provided to the controller 464 (e.g., via a wired or wireless connection).

The at least one recording electrode 468 is, in general, an extra-cochlear electrode (e.g., located outside of the cochlear). However, the at least one recording electrode 468 may be disposed at a number of locations within the recipient so to record the auditory evoked responses.

The controller 464 is also configured to cause the secondary stimulation device 466 to deliver the secondary stimulation (e.g., mechanical vibration, acoustic stimulation, etc.) to the ear of the recipient. The at leak one recording electrode 468 and the biopotential amplifier 470 are also configured to record the second auditory evoked responses evoked at/in the recipient in response to the secondary stimulation delivered via the secondary stimulation device 466. In the embodiment of FIG. 4, the recorded second auditory evoked responses are provided to the controller 464 (e.g., via a wired or wireless connection).

The controller 464 comprises one or more processors 465 that are configured to analyze the first and second auditory evoked responses to determine the equivalent sound pressure level for the actuator 424 and the mechanical coupling 446 and the efficiency of the combination of actuator 424 and the mechanical coupling 446 of the actuator 424 to the auditory structure. Similar to the above embodiments, the one or more processors 465 may also use the first and second auditory evoked responses and/or the equivalent sound pressure level to calculate the maximum gain and output level that the implantable acoustic hearing prosthesis 400 will provide.

In example embodiment of FIG. 4, the at least one recording electrode 468 and the biopotential amplifier 470 are generally separate from the implantable acoustic hearing prosthesis 400. FIG. 5 illustrates an alternative embodiment in which an implantable acoustic hearing prosthesis 500 includes both at least one recording electrode 568 and a biopotential amplifier 570.

More specifically, FIG. 5 illustrates a system 562 that comprises a controller 564, the implantable acoustic hearing prosthesis 500, and a secondary stimulation device 566. In the embodiment of FIG. 5, the implantable acoustic hearing prosthesis 500 includes an actuator 524 that is mechanically coupled to an auditory structure (not shown in FIG. 5) of a recipient's ear (also not shown in FIG. 5) via mechanical coupling 546. The implantable acoustic hearing prosthesis 500 also comprises the at least one recording electrode 568 and the biopotential amplifier 570. The controller 564 may be a computing device that is configured to communicate (e.g., via wired or wireless connections) with the implantable acoustic hearing prosthesis 500 and the secondary stimulation device 566.

The controller 564 is configured to cause the implantable acoustic hearing prosthesis 500 to deliver mechanical stimulation to the auditory structure via the actuator 524 and the mechanical coupling 546 (e.g., the controller 564 causes/instructs the implantable acoustic hearing prosthesis 500 to drive the actuator 524 at a known voltage, current, power, etc.). Simultaneously to the delivery of the mechanical stimulation, the implantable acoustic hearing prosthesis 500 is configured to use the at least one recording electrode 568 and the biopotential amplifier 570 to record the first auditory evoked responses evoked at/in the recipient in response to the mechanical stimulation delivered via the actuator 524. In the embodiment of FIG. 5, the recorded first auditory evoked responses are provided to the controller 564 (e.g., via the wired or wireless connection with the implantable acoustic hearing prosthesis 500).

The controller 564 is also configured to cause the secondary stimulation device 566 to deliver the secondary stimulation (e.g., mechanical vibration, acoustic stimulation, etc.) to the ear of the recipient. Again, when the secondary stimulation is delivered to the ear of the recipient, the implantable acoustic hearing prosthesis 500 is configured to use the at least one recording electrode 568 and the biopotential amplifier 570 to record the second auditory evoked responses evoked at/in the recipient in response to the secondary stimulation delivered via the secondary stimulation device 566. In the embodiment of FIG. 5, the recorded second auditory evoked responses are also provided to the controller 564 (e.g., via the wired or wireless connection with the implantable acoustic hearing prosthesis 500).

The controller 564 comprises one or more processors 565 that are configured to analyze the first and second auditory evoked responses to determine the equivalent sound pressure level for the actuator 524 and the mechanical coupling 546 and the relative efficiency of the combination of the actuator 524 and the mechanical coupling 546 of the actuator 524 to the auditory structure. Similar to the above embodiments, the one or more processors 565 may also use the first and second auditory evoked responses and/or the equivalent sound pressure level to calculate the maximum gain and output level that the implantable acoustic hearing prosthesis 500 will provide.

FIG. 6 illustrates another system 662 that comprises a controller 664, the implantable acoustic hearing prosthesis 600, and a secondary stimulation device 666. In the embodiment of FIG. 6, the acoustic hearing prosthesis 600 includes an actuator 624 that is mechanically coupled to an auditory structure (not shown in FIG. 6) of a recipient's ear (also not shown in FIG. 6) via mechanical coupling 646. The implantable acoustic hearing prosthesis 600 also includes at least one recording electrode 668, and a biopotential amplifier 670. Similarly, the secondary stimulation device 666 also includes at least one recording electrode 669 and a biopotential amplifier 677. The controller 664 may be a computing device that is configured to communicate (e.g., via wired or wireless connections) with the implantable acoustic hearing prosthesis 600 and a secondary stimulation device 666.

The controller 664 is configured to cause the implantable acoustic hearing prosthesis 600 to deliver mechanical stimulation to the auditory structure via the actuator 624 and the mechanical coupling 646 (e.g., the controller 664 causes/instructs the implantable acoustic hearing prosthesis 600 to drive the actuator 624 at a known voltage, current, power, etc.). Simultaneously to the delivery of the mechanical stimulation, the implantable acoustic hearing prosthesis 600 is configured to use the at least one recording electrode 668 and the biopotential amplifier 670 to record the first auditory evoked responses evoked at/in the recipient in response to the mechanical stimulation delivered via the actuator 624. In the embodiment of FIG. 6, the recorded first auditory evoked responses are provided to the controller 664 (e.g., via the wired or wireless connection with the implantable acoustic hearing prosthesis 600).

The controller 664 is also configured to cause the secondary stimulation device 666 to deliver the secondary stimulation (e.g., mechanical vibration, acoustic stimulation, etc.) to the ear of the recipient. Simultaneously to the delivery of the secondary stimulation, the secondary stimulation device 666 is configured to use the at least one recording electrode 669 and the biopotential amplifier 677 to record the second auditory evoked responses of the recipient in response to the secondary stimulation. In the embodiment of FIG. 6, the recorded second auditory evoked responses are provided to the controller 664 (e.g., via the wired or wireless connection with the secondary stimulation device 666).

The controller 664 comprises one or more processors 665 that are configured to analyze the first and second auditory evoked responses to determine the equivalent sound pressure level for the actuator 624 and the mechanical coupling 646 and the relative efficiency of the combination of the actuator 624 and the mechanical coupling 646 of the actuator 624 to the auditory structure. Similar to the above embodiments, the one or more processors 665 may also use the first and second auditory evoked responses and/or the equivalent sound pressure level to calculate the maximum gain and output level that the implantable acoustic hearing prosthesis 600 will provide.

FIG. 6 illustrates an embodiment that may be used for averaging multiple sweeps of stimulus and response in order to make the auditory evoked responses detectable above the noise floor. In particular, the arrangement of FIG. 6 enables the stimulus generation and response recording to be synchronized, e.g. occur with a fixed or no delay.

Figure 7:
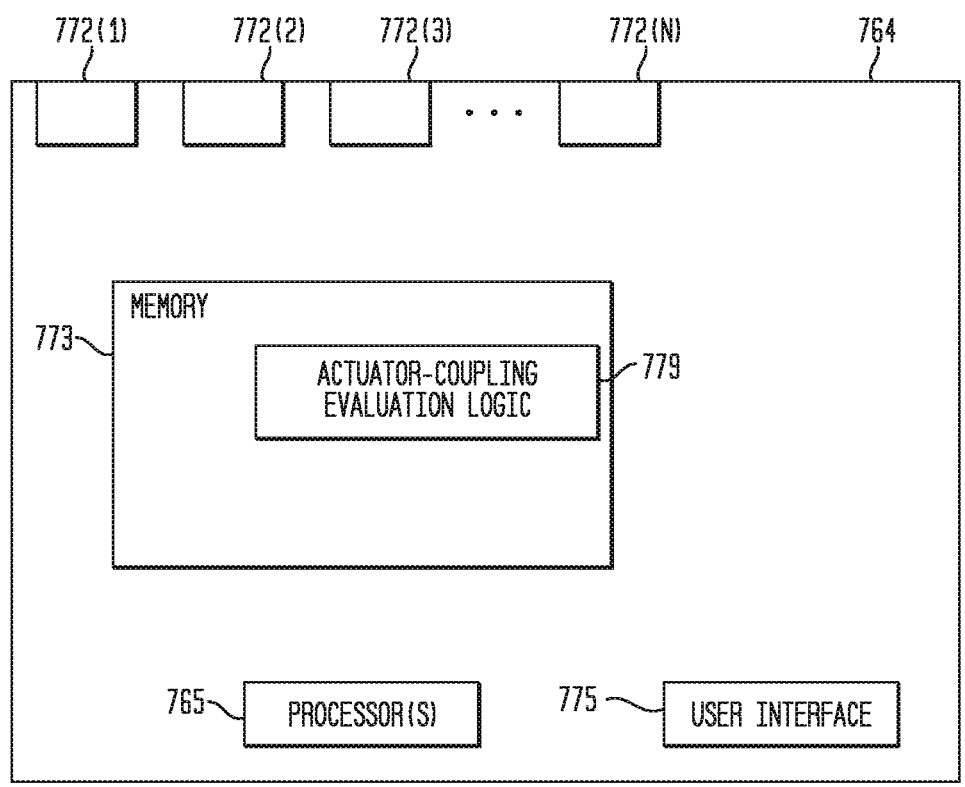
FIG. 7 is block diagram illustrating a controller, in accordance with certain embodiments presented herein.

FIG. 7 is a schematic block diagram illustrating an example arrangement for a controller, such as the controllers 464, 564, or 664 of FIGS. 4, 5, and 6, respectively, in accordance with certain embodiments presented herein. More specifically, shown in FIG. 7 is a controller 764 implemented as a computing device that comprises a plurality of interfaces/ports 772(1)-772(N), a memory 773, one or more processors 765, and a user interface 775. The interfaces 772(1)-772(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 7, one or more of the 772(1)-772(N) are configured for wired or wireless communication with an implantable acoustic hearing prosthesis (not shown in FIG. 7) having components implanted in a recipient, a secondary stimulation device (also not shown in FIG. 7) and, in certain embodiments, a biopotential amplifier. The interfaces 772(1)-772(N) may be directly connected to the implantable acoustic hearing prosthesis, the secondary stimulation device, and/or a biopotential amplifier, or connected one or more intermediary devices that are in communication with the implantable acoustic hearing prosthesis, the secondary stimulation device, and/or the biopotential amplifier.

The user interface 775 includes one or more output devices, such as a liquid crystal display (LCD) and a speaker, for presentation of visual or audible information/indications to a surgeon or other user. The user interface 775 may also comprise one or more input devices that include, for example, a keypad, keyboard, mouse, touchscreen, etc. that can accept a user input.

The memory 773 comprises actuator-coupling evaluation logic 779 that may be executed to perform operations of a controller, as described elsewhere herein. It would be appreciated that memory 773 may include other logic elements that, for ease of illustration, have been omitted from FIG. 7.

Memory 773 may comprise read only memory (ROM), random access memory (RAM), magnetic disk storage media devices, optical storage media devices, flash memory devices, electrical, optical, or other physical/tangible memory storage devices. The one or more processors 765 may be, for example, one or more microprocessors or microcontrollers that execute instructions for the actuator-coupling evaluation logic 779. Thus, in general, the memory 773 may comprise one or more tangible (non-transitory) computer readable storage media (e.g., a memory device) encoded with software comprising computer executable instructions and when the software is executed (by the one or more processors 765) it is operable to perform operations described herein.

It is to be appreciated that the arrangement for controller 764 shown in FIG. 7 is illustrative and that a controller in accordance with embodiments presented herein may include any combination of hardware, software, and firmware configured to perform the functions described herein. For example, controllers in accordance with embodiments presented herein may be personal computers, handheld devices (e.g., a tablet computer), a mobile devices (e.g., a mobile phone), and/or any other electronic device having the capabilities to perform the associated operations described elsewhere herein.

FIG. 8 is a flowchart of another method 880 in accordance with embodiments presented herein that may implemented by, for example, the systems of FIG. 4, 5, or 6. Method 880 begins at 882 where an actuator implanted in a recipient and mechanically coupled to an auditory structure of an ear of the recipient delivers mechanical stimulation to the auditory structure to cause a pressure change in an inner ear of the recipient. At 884, a secondary stimulation device delivers secondary stimulation to the ear of the recipient to cause a pressure change in an inner ear of the recipient. At 886, a recording electrode and biopotential amplifier disposed in the recipient perform first and second sets of objective measurements of potentials evoked in response to the mechanical stimulation and the secondary stimulation, respectively. At 888, a controller determines, based on the first and second sets of objective measurements, an efficiency of the combination of the actuator and the mechanical coupling of the actuator to the auditory structure.

As noted above, presented herein are techniques for analyzing intra-operatively auditory evoked responses/potentials to both mechanical stimulation (e.g., via an implantable acoustic hearing prosthesis) and to secondary stimulation (e.g., acoustic or bone conduction stimulation) in order to determine an equivalent sound pressure level (e.g., the recorded evoked potentials are correlated to the loudness perception the recipient would have if awake). The equivalent sound pressure level is used to determine a vibratory coupling efficiency (e.g., an efficiency of the combination of the actuator and the mechanical coupling of the actuator to an auditory structure of the recipient's ear). In certain examples, the equivalent sound pressure level is used to estimate/predict absolute performance (gain, output) of the implantable acoustic hearing prosthesis and to identify audiological needs of the recipient.

It is to be appreciated that the embodiments presented herein are not mutually exclusive. The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   delivering, with an actuator implanted in a recipient and mechanically coupled to an auditory structure of an ear of the recipient, mechanical stimulation to the auditory structure to effect a pressure change in an inner ear of the recipient;
   capturing one or more first auditory evoked responses of the recipient to the mechanical stimulation;
   delivering, with one or more stimulation devices that are separate from the actuator, secondary stimulation to the recipient to effect a pressure change in the inner ear of the recipient;
   capturing one or more second auditory evoked responses of the recipient to the secondary stimulation; and
   determining, using the one or more first auditory evoked responses and the one or more second auditory evoked responses, an efficiency of a combination of the actuator and the mechanical coupling of the actuator to the auditory structure.

2. The method of claim 1, wherein the actuator is driven at a predetermined level to generate the mechanical stimulation, and wherein determining the efficiency of the actuator and the mechanical coupling to the auditory structure comprises:
   determining a level of the secondary stimulation at which a first parameter of the one or more second auditory evoked responses is approximately equivalent to a same first parameter of the one or more first auditory evoked responses.

3. The method of claim 2, wherein the first parameter is an amplitude parameter associated with each of the one or more first auditory evoked responses and the one or more second auditory evoked responses.

4. The method of claim 2, wherein the first parameter is a latency associated with each of the one or more first auditory evoked responses and the one or more second auditory evoked responses, wherein the latency is a time period between delivery of a stimulation and an occurrence of an auditory evoked response to the delivered stimulation.

5. The method of claim 1, further comprising:
   comparing the efficiency of the actuator and the mechanical coupling to the auditory structure to normative data.

6. The method of claim 1, wherein the actuator is a component of an implantable auditory prosthesis comprising a sound sensor, and wherein the method further comprises:
   estimating, based on the efficiency of the actuator and the mechanical coupling to the auditory structure, a maximum achievable gain of the implantable auditory prosthesis for sound signals captured at the sound sensor.

7. The method of claim 1, further comprising:
   based on the efficiency of the actuator and the mechanical coupling to the auditory structure, adjusting the mechanical coupling between the actuator and the auditory structure of the ear of the recipient.

8. The method of claim 1, wherein delivering the mechanical stimulation to the recipient comprises:
   delivering the mechanical stimulation to a middle ear bone of the recipient.

9. The method of claim 1, wherein delivering the mechanical stimulation to the recipient comprises:
   delivering the mechanical stimulation to at least one of a round window or oval window of the inner ear of the recipient.

10. The method of claim 1, wherein delivering the secondary stimulation to the recipient comprises:
    delivering acoustical stimulation to the ear of the recipient.

11. The method of claim 1, wherein delivering the secondary stimulation to the recipient comprises:
    delivering mechanical vibration to a skull bone of the recipient.

12. The method of claim 1, wherein the actuator is a component of an implantable auditory prosthesis comprising a sound sensor, and wherein the method comprises:
    capturing the one or more first auditory evoked responses via the implantable auditory prosthesis; and
    capturing the one or more second auditory evoked responses via the implantable auditory prosthesis.

13. The method of claim 1, wherein the actuator is a component of an implantable auditory prosthesis comprising a sound sensor, and wherein the method comprises:
    capturing the one or more first auditory evoked responses via the implantable auditory prosthesis; and
    capturing the one or more second auditory evoked responses via a device that is separate from the implantable auditory prosthesis.

14. A system, comprising:
    an actuator implanted in a recipient and mechanically coupled to an auditory structure of an ear of the recipient, wherein the actuator is configured to deliver mechanical stimulation to the auditory structure to cause a pressure change in an inner ear of the recipient;
    a secondary stimulation device configured to deliver secondary stimulation to the ear of the recipient to cause a pressure change in an inner ear of the recipient;
    at least one recording electrode and at least one biopotential amplifier configured to capture a first set of auditory evoked responses evoked at the inner ear of the recipient in response to the mechanical stimulation and to capture a second set of auditory evoked responses associated with the inner ear of the recipient and evoked in response to the secondary stimulation; and
    a controller configured to determine, using the first set of auditory evoked responses and the second sets of auditory evoked responses, an equivalent sound pressure level associated with operation of the actuator.

15. The system of claim 14, wherein the equivalent sound pressure level is a level of the secondary stimulation at which a first parameter of the second set of auditory evoked responses is approximately equivalent to a same first parameter of the first set of auditory evoked responses.

16. The system of claim 15, wherein the first parameter is an amplitude parameter associated with each of the first set of auditory evoked responses and the second set of auditory evoked responses.

17. The system of claim 15, wherein the first parameter is a latency associated with each of the first set of auditory evoked responses and the second set of auditory evoked responses, wherein the latency is a time period between delivery of a stimulation and an occurrence of an auditory evoked response to the delivered stimulation.

18. The system of claim 14, wherein the controller is configured to:
determine, based on the equivalent sound pressure level associated with operation of the actuator, an efficiency of a combination of the actuator and the mechanical coupling of the actuator to the auditory structure.

19. The system of claim 18, wherein the controller is configured to:
initiate a comparison of the efficiency of the actuator and the mechanical coupling to the auditory structure to normative data.

20. The system of claim 18, wherein the actuator is a component of an implantable auditory prosthesis at least partially implanted in the recipient and comprising a sound sensor, and wherein the controller is configured to:
estimate, based on the efficiency of the actuator and the mechanical coupling to the auditory structure, a maximum achievable gain of the implantable auditory prosthesis for sound signals captured at the sound sensor.

21. The system of claim 14, wherein the at least one recording electrode, the at least one biopotential amplifier, and the actuator are each part of an implantable auditory prosthesis.

22. The system of claim 14, wherein the at least one recording electrode comprises a plurality of recording electrodes, and wherein at least two of the plurality of recording electrodes are disposed in separate devices.

23. A method, comprising:
delivering, via an actuator implanted in a recipient and mechanically coupled to an auditory structure of an ear of the recipient, mechanical stimulation to the auditory structure to cause a pressure change in an inner ear of the recipient;
delivering, via a secondary stimulation device, secondary stimulation to the ear of the recipient to cause a pressure change in an inner ear of the recipient;
performing first and second sets of objective measurements evoked in response to the mechanical stimulation and the secondary stimulation, respectively; and
determining, based on the first and second sets of objective measurements, a combined efficiency of the actuator and the mechanical coupling of the actuator to the auditory structure.

24. The method of claim 23, wherein the actuator is driven at a predetermined voltage to generate the mechanical stimulation, and wherein determining the efficiency of the actuator and the coupling to the auditory structure comprises:
determining a level of the secondary stimulation at which a first parameter of the second set of objective measurements evoked in response to the secondary stimulation is approximately equivalent to a same first parameter of the first set of objective measurements evoked in response to the mechanical stimulation.

25. The method of claim 24, wherein the first parameter is an amplitude parameter associated with the second set of objective measurements evoked in response to the secondary stimulation and the first set of objective measurements evoked in response to the mechanical stimulation.

26. The method of claim 24, wherein the first parameter is a latency associated with the second set of objective measurements evoked in response to the secondary stimulation and the first set of objective measurements evoked in response to the mechanical stimulation, wherein the latency is a time period between delivery of a stimulation and an occurrence of an inner ear response to the delivered stimulation.

27. The method of claim 23, further comprising:
comparing the efficiency of the actuator and the mechanical coupling to the auditory structure to normative data.

28. The method of claim 23, wherein the actuator is a component of an implantable auditory prosthesis comprising a sound sensor, and wherein the method further comprises:
estimating, based on the efficiency of the actuator and the mechanical coupling to the auditory structure, a maximum achievable gain of the implantable auditory prosthesis for sound signals captured at the sound sensor.

29. The method of claim 23, further comprising:
based on the efficiency of the actuator and the mechanical coupling to the auditory structure, adjusting the mechanical coupling between the actuator and the auditory structure of the ear of the recipient.

* * * * *

UNITED STATES PATENT AND TRADEMARK OFFICE
CERTIFICATE OF CORRECTION

| | |
|---|---|
| PATENT NO. | : 11,272,297 B2 |
| APPLICATION NO. | : 16/969369 |
| DATED | : March 8, 2022 |
| INVENTOR(S) | : Bernd Waldmann et al. |

It is certified that error appears in the above-identified patent and that said Letters Patent is hereby corrected as shown below:

In the Claims

Claim 14, Column 16, Line 63, replace "the second sets of" with --the second set of--

Signed and Sealed this
Seventeenth Day of May, 2022

*Katherine Kelly Vidal*

Katherine Kelly Vidal
*Director of the United States Patent and Trademark Office*